United States Patent [19]

Tracy et al.

[11] Patent Number: 5,300,665
[45] Date of Patent: Apr. 5, 1994

[54] PROCESS FOR PREPARING FATTY ACID ESTERS AND AMIDES OF SULFONIC ACID SALTS

[75] Inventors: David J. Tracy, Plainsboro, N.J.; Mitchell B. Ferguson, Winder, Ga.; Gordon Wall, Newton, N.J.

[73] Assignee: Rhone-Poulenc Surfactants and Specialties, L.P., Princeton, N.J.

[21] Appl. No.: 946,269

[22] Filed: Sep. 16, 1992

[51] Int. Cl.⁵ ............................. C07C 143/90
[52] U.S. Cl. ........................... 554/49; 554/92; 568/31
[58] Field of Search ............. 554/49, 92; 568/31

[56] References Cited

U.S. PATENT DOCUMENTS

| | | | |
|---|---|---|---|
| Re. 23,823 | 5/1954 | Molteni et al. | 554/92 |
| 2,303,582 | 10/1938 | Russell et al. | 260/400 |
| 2,307,953 | 1/1943 | Potter | 260/459 |
| 2,316,719 | 4/1943 | Russell | 260/400 |
| 2,810,747 | 10/1957 | Sexton et al. | 260/513 |
| 2,820,818 | 1/1958 | Sexton et al. | 260/513 |
| 2,857,370 | 10/1958 | Sundberg | 260/97.5 |
| 2,880,219 | 3/1959 | Burnette et al. | 260/401 |
| 2,898,352 | 8/1959 | Schenck | 260/400 |
| 2,923,724 | 2/1960 | Anderson et al. | 260/400 |
| 2,974,153 | 3/1961 | Gajewski et al. | 260/401 |
| 2,974,154 | 3/1961 | Schenck | 260/401 |
| 3,004,049 | 10/1961 | Schenck | 260/406 |
| 3,150,156 | 9/1964 | Lamberti | 260/401 |
| 3,151,136 | 9/1964 | Koczorowski et al. | 260/400 |
| 3,232,968 | 12/1959 | Schenck et al. | 260/401 |
| 3,234,247 | 5/1962 | Abend et al. | 260/401 |
| 3,320,292 | 5/1967 | Cahn et al. | 260/400 |
| 3,383,396 | 5/1968 | Cahn et al. | 260/400 |
| 3,394,155 | 7/1968 | Cahn et al. | 260/400 |
| 3,420,857 | 1/1969 | Holland et al. | 554/92 |
| 3,420,858 | 1/1969 | McCrimlisk et al. | 554/92 |
| 3,429,136 | 2/1969 | Holt et al. | 554/92 |
| 3,745,181 | 7/1973 | Wrigley et al. | 260/400 |
| 3,880,897 | 4/1975 | Landy | 260/400 |
| 4,476,055 | 10/1984 | Du Vernet | 260/400 |
| 4,515,721 | 5/1985 | Login et al. | 554/92 |
| 4,536,338 | 8/1985 | Urban et al. | 554/92 |
| 4,537,724 | 8/1985 | McKinnie et al. | 260/400 |
| 5,121,611 | 6/1992 | Broderdorf et al. | 62/374 |

*Primary Examiner*—José G. Dees
*Assistant Examiner*—Samuel Barts
*Attorney, Agent, or Firm*—Paul J. Juettner

[57] ABSTRACT

Fatty acid esters of hydroxyalkylsulfonates and fatty acid amides of aminoalkylsulfonates are prepared by heating an excess of the fatty acids with the sulfonate until the water of condensation is removed. The excess fatty acid is removed by distillation and the isolated fatty acid ester or amide product is directly and rapidly cooled to minimize decomposition and color degradation.

20 Claims, No Drawings

PROCESS FOR PREPARING FATTY ACID ESTERS AND AMIDES OF SULFONIC ACID SALTS

The invention relates to a process for the preparation of esters or amides having the general formula RCOXR'SO$_3$M. In this formula, R represents the aliphatic hydrocarbon residue of a fatty acid or a fatty acid ester containing from 6 to 24 carbon atoms, R' represents a divalent hydrocarbon radical containing from 2 to 4 carbon atoms, X represents oxygen or N-R" where R" represents hydrogen or a C$_1$-C$_7$ alkyl, and M represents an alkali metal cation. These compounds, prepared by reacting a fatty acid, fatty acid ester or mixtures thereof with a hydroxyalkylsulfonate or aminoalkylsulfonate, are well known as valuable detergents and wetting agents.

BACKGROUND OF THE INVENTION

The preparation of said esters by the direct esterification of the fatty acid with the hydroxyalkylsulfonate and said amides by the amidification of the fatty acid with the aminoalkylsulfonate has presented difficulties because of the high temperature required to obtain suitable conversion. At the temperatures required for the direct esterification and amidification reactions, usually in the range of 200° to 250° C., the hot reaction product rapidly loses activity and degrades in color. Various methods are taught in the art to avoid loss in activity and color degradation of the reaction product.

Several patents teach the desirability of accelerating the reaction. Sundberg in U.S. Pat. No. 2,857,370 teaches the use of a boron-containing compound as a catalyst at reduced pressure or in an inert atmosphere. Anderson et al. in U.S. Pat. No. 2,923,724 disclose the use of a phosphorus containing compound such as phosphoric acid or phosphate as an accelerator. In U.S. Pat. No. 3,151,136, Koczorowski et al. teach that quantitative yields may be obtained at relatively low temperatures by using hydroxyalkylsulfonic acid which is substantially free from its salts, while operating at reduced pressure. The reaction product in this case must be neutralized to obtain the desired metal salt, introducing a further step. Zinc and zirconium salts are disclosed as catalysts for the esterification reaction by Cahn in U.S. Pat. No. 3,320,292 and U.S. Pat. No. 3,383,396, respectively.

A number of prior art patents teach the use of modifications of the fatty acid to improve the reactivity. For example, Schenck in U.S. Pat. No. 2,898,352 teaches the use of a mixed borate-fatty acid anhydride. This patent further teaches that the resulting borax may be removed from the reaction product by filtration of the molten product or by solvent extraction, using either organic solvents such as hydrocarbons, alcohols or esters to remove the fatty acid isethionic acid esters or aqueous extractions to remove the borax and sodium isethionate. Wrigley et al. in U.S. Pat. No. 3,745,181 describe the use of isopropanol fatty esters to react with hydroxyalkylsulfonate salts.

Several of the patents already mentioned also teach the desirability of maintaining a nitrogen atmosphere in order to avoid oxidation of the reaction product and also the use of reduced pressure to permit the removal of water formed during condensation at a lower temperature.

A number of patents teach a method by which the reaction product is purified so as to remove the unreacted fatty acid, sulfonate or mixture thereof that is typically present. McCrimlisk in U.S. Pat. No. 3,420,858 teaches the removal of lower fatty acids by a two-stage vacuum stripping, in which higher fatty acids are added to the reaction mixture after some of the lower acids have been removed, in order to maintain fluidity and to make possible the further removal of the lower fatty acids. Molteni in U.S. Pat. No. Patent Re. 23,823 uses an excess of sodium isethionate in his reaction and removes the excess after the esterification has taken place by dispersing the product in water, evaporating and precipitating out the desired fatty acid ester. Russell et al. in U.S. Pat. No. 2,303,582, Potter in U.S. Pat. No. 2,307,953, and Russell in U.S. Pat. No. 2,316,719 all describe methods for separating inorganic salts from organic sulfonates or sulfates by forming two-phase liquid systems in which the inorganic salt is in aqueous solution and the organic compound is dissolved in an organic solvent, which may be an alcohol such as isopropanol. The aqueous layer is drawn off to remove the inorganic salt. Landy in U.S. Pat. No. 3,880,897 describes a process in which a hydroxyalkyl sulfonate is reacted with a fatty acid halide in anhydrous dialkyl ketone. When the reaction is complete, the mixture is cooled and the insoluble ester is filtered from the dialkyl ketone solvent, washed and dried.

Holt et al. in U.S. Pat. No. 3,429,136 teach that degradation of the hot reaction product may be avoided by injecting cold water into the hot crude condensate to cool the mass below a temperature at which rapid discoloration would occur. A disadvantage of this method is that the addition of water can lead to an undesirable hydrolysis side reaction. Login et al. in U.S. Pat. No. 4,515,721 describe immersion of hot crude fatty acid ester in a liquid such as an alcohol solvent that is at a temperature lower than the crude reaction mixture to effect cooling of the reaction mixture. Cooling by this method requires the use of a liquid in which the ester is substantially insoluble and the unreacted fatty acid is soluble. A slurry is formed in which the solid phase comprises relatively pure ester and the liquid phase comprises the cooling liquid and unreacted fatty acid. The solid phase is thereafter separated from the liquid phase of the slurry, typically by filtration or by centrifugation. The filtrate is typically distilled to recover free fatty acid and cooling liquid. Hence, a disadvantage of this method is that it requires several process steps to cool and isolate the reaction product.

Urban et al. in U.S. Pat. No. 4,536,338 describe the use of an alkaline quenching material to neutralize the acid catalyst, thereby reducing or eliminating darkening and deterioration of the reaction product caused by severe stripping conditions.

All of the above mentioned citations as well as any other citations noted hereinbelow are understood to be incorporated by reference in toto into this disclosure.

SUMMARY OF THE INVENTION

It has now been found possible to prepare compounds of the class described above by a process which involves the direct esterification or amidification of the fatty acid with the hydroxyalkylsulfonate or aminoalkylsulfonate to yield a product having excellent color and activity. The process employs easily performed operations which strip the excess fatty acid from the reaction mixture under conditions which minimize any possible discoloration or degradation of the reaction product and which provide for direct, rapid cooling of the reaction product, giving a desirable product having good color and high activity.

It is an object of the present invention to provide a process for producing fatty acid esters or amides that are directly and rapidly cooled, that utilizes controlled distillation conditions and simply and economically isolates the reaction product, without the need to inject water into the hot reaction product or to immerse the hot reaction product in water, and at the same time Minimizing color generation and decomposition and producing fatty acid esters or amides having high activity.

Other objects and advantages will appear as the description proceeds.

DETAILED DESCRIPTION OF THE INVENTION

The process of the present invention comprises reacting a fatty acid, fatty acid ester or mixtures thereof with a hydroxyalkyl sulfonate or aminoalkylsulfonate, distilling off water formed during the reaction, removing excess fatty acid, and rapidly cooling and directly isolating the reaction product.

Suitable fatty acids for use in the process of this invention are those containing from 6 to 24 carbon atoms. They include the unsubstituted, saturated or unsaturated straight-chain or branched chain fatty acids, such as those derived from coconut, palm kernel and babassu oils. Such fatty acids are available in a variety of grades. When derived from naturally occurring oils, they usually comprise a mixture of fatty acids of varying chain lengths. If higher molecular weight reaction mixtures are desired, then fatty acids derived from glycerides which contain palmitic or stearic acids may be employed, for example those derived from tallow, soybean, rapeseed, tall oil and sunflower oils. Either unsaturated or saturated compositions can be employed, but the latter will afford lighter colored reaction mixtures. Fatty acids derived from coconut oil, comprising a mixture of $C_8$ to $C_{18}$ fatty acids and oleic acid represent preferred fatty acid reactants.

The hydroxyalkylsulfonate used in the reaction, commonly referred to as an isethionate salt, has the general formula $HOR'SO_3M$. The divalent hydrocarbon radical $R'$ contains 2 to 4 carbon atoms, and is typically, ethylene, methylethylene, dimethylethylene, propylene or butylene. M is an alkali metal cation, preferably sodium or potassium. The preparation of isethionate salts is well known to those skilled in the art and is described for example in U.S. Pat. No. 2,810,747 and U.S. Pat. No. 2,820,818. Although the divalent alkyl radical $R'$ can be branched, the straight-chain radicals are preferred since they tend to have greater thermal stability and will degrade in color to a lesser extent at the high temperatures necessary for the condensation reaction. Preferred compounds are sodium isethionate, potassium isethionate and sodium 3-hydroxpropane sulfonate.

The aminoalkylsulfonate used in the reaction has the general formula

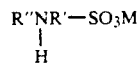

wherein $R''$, $R'$ and M are defined above.

The amount of fatty acid introduced into the reaction mixture should be in molar excess in relation to the hydroxyalkyl sulfonate or aminoalkylsulfonate. Preferably the molar ratio of fatty acid to sulfonate should be at least about 1.1:1 but not higher than about 2:1. Excess fatty acid helps to maintain the reaction mixture in liquid form. If less than 1.1:1 moles of fatty acid per mole of sulfonate is used, the mixture may become difficult to stir and almost impossible to transfer. Excess fatty acid also tends to force the reaction to go forward, thus resulting in a high utilization of the hydroxyalkylsulfonate or aminoalkylsulfonate. The optimum amount of excess fatty acid will vary somewhat according to the particular fatty acid and hydroxyalkylsulfonate or aminoalkylsulfonate that is used. Excess fatty acid is removed during the distillation step.

The reaction should be carried out in a substantially oxygen-free atmosphere, since oxygen will rapidly darken the product at elevated temperatures. It is thus desirable to maintain an inert gas atmosphere and this is conveniently done by sparging with nitrogen throughout the course of the reaction. The sparging is also beneficial in helping to agitate the reaction mixture and to sweep out water vapor and some unreacted fatty acid.

It is convenient, but not required, to add the hydroxyalkyl sulfonate or aminoalkylsulfonate in aqueous solution. The water so added, together with the water formed during the reaction, is distilled off during the heating period. During this step, the temperature is gradually raised to between about 200° and 250° C. and maintained in this range until the water has been removed. Free, unreacted fatty acid also distills off at this elevated temperature and the distilled fatty acid can be recycled. The progress of the reaction may be followed by checking the free fatty acid content and measuring the activity of the reaction mixture.

In order to reduce the temperature and time required for the reaction, any suitable promoter may be employed. Such promoters are well known in the art, and typically include, for example, sodium hypophosphite, sodium orthophosphate, sodium borate or a combination thereof, and preferably zinc oxide.

When the reaction is complete, the molten, crude reaction mixture is distilled to effect rapid separation of the sulfonated fatty acid ester or amide from unreacted fatty acid and other impurities.

Distillation of the reaction mixture maybe conducted in a kettle reactor. In the kettle distillation method, vacuum of 0.1 to 50mm Hg at a temperature between about 200° and 300° C. is applied and the distillation is performed for 0.5 to 10 hours. Preferably, the kettle distillation is conducted at a vacuum of 1 to 10 mm Hg and a temperature between about 210° and 235° C., for 1 to 4 hours.

Distillation may be conducted in a thin film evaporator. The distillation in the thin film evaporator is typically conducted at an evaporator temperature between about 200° and 300° C., a vacuum of 50mm Hg or less, a ratio of feed per unit surface area of 10 to 75 lbs. per sq. ft. hr. Preferably, the thin film distillation is conducted at a temperature between about 230° and 290° C., a vacuum of between 1 and 5mm Hg, and a ratio of feed per unit surface area of 35 to 55 lbs. per sq. ft. hr.

The hot reaction mixture is discharged from the distillation unit and transferred to a cooling unit. This transfer should be carried out as quickly as possible, consistent with avoiding local overheating of the liquid. At the cooling unit, the temperature of the reaction product is rapidly decreased to minimize degradation and product decomposition. A rotary drum flaker or a belt flaker is preferably used to effectuate rapid cooling.

In the belt flaker method of rapid cooling, reaction product is continuously and uniformly dispersed over the belt surface by overhead feeding. Cooling water or glycol water at a temperature between about 0° and 40° C., preferably between about 10° and 20° C., is contacted on the underside of the belt, allowing for rapid heat transfer from the hot product to the cooling medium. The product solidifies upon cooling and is continuously removed from the outer surface of the belt by a stationary flaking knife which has been set a prescribed distance from the shell of the drum.

An alternative method of rapid cooling employs a rotary drum flaker. Reaction product is dispersed continuously and uniformly over the surface of the drum by dipping the drum into a feed pan or alternatively by overhead feeding. The drum is contacted on the interior wall by cooling water, glycol water or a cryogenically-cooled liquid, such as d-limonene, at a temperature between about 450° and 40° C., preferably between about −30° and 20° C., providing rapid heat transfer from the hot product to the cooling medium. The product solidifies upon cooling and is continuously removed from the surface of the drum by a stationary flaking knife which has been set at a prescribed distance from the drum surface.

The present invention provides a process for the preparation of sodium cocyl isethionate (Igepon A). According to this process, coconut fatty acids and sodium isethionate in solid form or aqueous solution are reacted in the presence of zinc oxide. The mole ratio of fatty acid to isethionate is 1.25 and the reaction is conducted at 240° C. with removal of water of reaction by distillation. After the activity of the reaction mixture reaches 65 to 69%, the reaction mixture is pumped to a thin film reactor to remove residual fatty acid by thin film distillation. The thin film distillation is conducted at 290° C. and at 1 to 5 mm of Hg, and product exits from the reactor to a cooling drum or flaker. The resulting product is 85 to 95% active.

Another embodiment of the present invention provides a process for the preparation of sodium oleoyl N-methyltaurate (IGEPON T). The process includes reacting oleic acid and sodium N-methyltaurate (solid or solution) in the presence of catalytic quantities of a reaction promoter such as sodium orthophosphite, sodium hypophosphite or sodium borate. A molar ratio of oleic acid to taurinate of 1.5.:1 is used and the reaction is conducted at 240° C. with the removal of water of reaction by distillation. After the activity of the reaction mixture reaches 65 to 704, the reaction mixture is transferred to a thin film evaporator to remove residual oleic acid by thin film distillation. The thin film distillation is conducted at 2900C and at 1 to 5mm of Hg, and product exits from the evaporator to a cooling drum or belt flaker. The resulting product is 85 to 95% active.

The following examples illustrate the operation of this invention, and are not intended to limit the invention.

EXAMPLE I

PREPARATION OF SODIUM COCOYL ISETHIONATE

To a 3 liter hot oil jacketed resin pot equipped with a double turbine agitator, thermometer, fritted glass sparge tube and distillation take off, charge 446.0 g coconut fatty acid (Procter & Gamble, C-108, acid number 269) and 197.0 g sodium isethionate (Rhone-Poulenc, 97% pure by HPLC, 0.4% glycol, 0.275% $H_2O$) and 1.0 g zinc oxide (Aldrich Chem. Co.). Heat the reaction slowly to 230°-240° C., removing water as it forms. Water carries off a small amount of fatty acid. The reaction can be followed by acid number and/or methylene blue (M.B.) titration. The water and acid separate and the acid can be recycled.

All the water is removed, usually in 3-5 hours, depending on the sparge rate and agitation. In this case, the reaction was held 4 hours between 218° and 238° C. During this time 21.5 g of water was collected.

Apply vacuum to the reactor to remove excess fatty acid. Fatty acid begins to boil at 75 to 80 mm of Hg, continuing down to about 10 mm of Hg. A total of 130 g of fatty acid was collected. Release the vacuum with nitrogen, and discharge the product onto a bed of dry ice over a 10 minute period. The distillation time required to remove excess coconut acid is 15 to 30 minutes. The product weighs 470 g. The product is 85% active by methylene blue (M.B.) analysis, containing 6.6% free fatty acid. The product loses 12% of its activity in 6 hours and 30% in 24 hours when held at 230° C. Stability studies are summarized below.

Stability Studies

Successful scale up requires transfer of the molten liquid product to a flaker or thin film evaporator. The operation necessitates holding the hot liquor until it can be transferred, thus assuming stability.

In as much as IGEPON A is very viscous and difficult to agitate, the temperature in a heated flask may not be uniform. Stability was studied at 180°, 200°, 215° and 230° C. in sealed tubes. The tubes were small, and consequently in most cases, two tubes were removed at each time and analyzed by methylene blue titration (M.B.). A crude IGEPON prior to removal of excess coconut acid was used to simulate the situation prior to passage through a thin film evaporator. The results are tabulated in Table I and show stability between 180° and 200° C. Higher temperatures result in significant decomposition. IGEPON A processing activities over 80% require temperatures in excess of 230° C. to remain molten. The use of a wiped film or thin film evaporator allows the product to be distilled to remove the fatty acid and then immediately cooled whereby a high activity product can be obtained.

TABLE I

| | HEAT STABILITY OF IGEPON A (SEALED TUBES) ACTIVITIES TIME | | | | |
|---|---|---|---|---|---|
| TEMP (°C.) | 3 HRS | 6 HRS | 22 HRS | 24 HRS | 30 HRS |
| 180 | | 71.9 | 70.2 | | 68.9 |
| | | 71.7 | 69.9 | | 71.3 |
| 200 | | 70.7 | | 68.9 | 67.7 |
| | | 71.0 | | 68.2 | 66.5 |
| 215 | 70.6 | 69.8 | 66.2 | | 62.1 |
| | 71.3 | | 66.3 | | 62.9 |
| | | | | | 62.2 |
| 230 | | 64.9 | | 52.6 | 45.3 |
| | | | | 51.5 | 47.0 |

EXAMPLE 2

PREPARATION OF SODIUM COCOYL ISETHIONATE

To a 5 liter flask equipped with an agitator, thermocouple, sparge tube and distillation take off, charge 223.0 g coconut fatty acid (Procter & Gamble Co., C-108) and 5.0 g zinc oxide. Heat the kettle to 200° C. and charge over 4 hours 179.0 g aqueous sodium isethionate (554 active, 98.4 g of of 100%). Water is allowed to distill during addition. After addition is complete, heat to 230° C. and hold 1 hour. Activity is monitored by acid number and two phase titration (methylene blue, M.B.) When reaction is complete, cool to 180°0 C. and transfer to an evaporator.

Evaporator

The feed is transferred to the circumference of a cylindrical tube. The material is spread evenly or uniformly. The tube is evacuated. The material flows down the heated cylinder and is spread thin by a rotor. The fatty acids are evaporated at the heated wall and travel upward through the annular space between the wall and the rotor. The vapors travel out of the evaporator and into a heat exchanger where they are condensed. The concentrated product is very viscous and is pumped from the bottom of the evaporator to a drum flaker, flaker belt or cryogenic flaker.

The thin film distillation described allows rapid distillation, thereby minimizing product decomposition and color build-up in the final product.

The above product was pumped through the evaporator at a wall temperature of 240° C. and 2 mm of pressure. The product is 85% active (M.B. on M.W. 338), containing 6% unreacted sodium isethionate, 1.2% sodium vinyl sulfonate and 5% coconut fatty acid. The product has a color of APHA 30 (5% in 15% Isopropanol - water).

EXAMPLE 3

PREPARATION OF SODIUM 2 - MYRISTOYLOXYETHANE SULFONATE

The titled product is made via the method of Example 2 by substituting 224.0 g of myristic acid for coconut acid. Heat the tube wall to 240° C. at 2 mm Hg. Isolate product 85% active by Methylene Blue analysis (M.W. 358).

EXAMPLE 4

PREPARATION OF SODIUM 2 - STEAROYLOXYETHANE SULFONATE

The titled product is prepared via the method of Example 2 by substituting 304.0 g stearic acid for coconut acid. The product is isolated by pumping through the evaporator at 300° C. and 1 mm of pressure. The product obtained was 88% active (M.W. 414).

EXAMPLE 5

PREPARATION OF SODIUM 2 - OLEOYLOXYETHANE SULFONATE

The titled product is prepared by the method of Example 2 by substituting 302.5 g oleic acid for coconut acid. The walls of the evaporator are adjusted to 300° C. and the pressure lowered to 1 mm. The product obtained was analyzed to be 87% active by methylene blue titration (M.W. 412).

EXAMPLE 6

PREPARATION OF SODIUM N - METHYL N - COCOYL TAURINATE

To a 3 liter hot oil jacketed resin pot equipped with a double turbine agitator, thermometer, fritted glass sparge tube and distillation take off, charge 461 g coconut fatty acid (Procter & Gamble, C-108), 15.9 g sodium hypophosphite monohydrate and 15.9 g sodium orthophosphite. Heat the reactor to 200° C. and charge over a four hour period by dropping funnel 666 g aqueous sodium N-methyltaurinate (38% active, 253 g of 100%). Water is allowed to distill off during the addition. Heat the reactor after addition is complete to 230° C. and hold 2.5 hours or until reaction is complete. Reaction is followed by methylene blue analysis. Upon completion the reactor is cooled to 180° -200° C. and pumped to the evaporator. Excess coconut acid is removed at 240° C. jacket temperature and 2 mm of Hg vacuum. The product is cooled on a flaker to yield the product. A product 90% active (N.W. 353) containing 5% free coconut fatty acid is obtained.

EXAMPLE 7

PREPARATION OF SODIUM N - METHYL-N - OLEOYL TAURINATE

The titled product is made by the procedure of Example 6 by substituting 623 g oleic acid for coconut acid. The jacket of the concentrator is adjusted to 300° C. and the vacuum reduced to 1 mm of Hg. Product 88% active (M.W. 425) is obtained.

EXAMPLE 8

PREPARATION OF SODIUM N - CYCLOHEXYL N - PALMITOYL TAURINATE

Synthesis is effected by the procedure of Example 6 by substituting 576 g palmitic acid for coconut acid and 1419 g (355 g 100%) aqueous sodium cyclohexyltaurinate for sodium N-methyltaurate. Concentration was effected at 285° C. and 1 mm of Hg vacuum. The yield is 850 g of 85% active (M.W. 467) product containing 6% residual fatty acid.

It will be understood that the foregoing examples and explanations are for illustrative purposes only and that in view of the instant disclosure various modifications of the present invention will be self-evident to those skilled in the art and are to be included within the spirit and purview of this application and the scope of the appended claims.

We claim:

1. A process for preparing a compound of formula (I)

$$RCOXR'SO_3M \qquad (I)$$

wherein:
R represents an aliphatic hydrocarbon residue of a fatty acid or a fatty acid ester containing from 6 to 24 carbon atoms,
R' represents a divalent hydrocarbon radical containing from 2 to 4 carbon atoms,
X represents oxygen or N-R" where R" represents hydrogen or a $C_1$-$C_7$ alkyl, and
M represents an alkali metal cation,
the steps consisting essentially of:
(a) heating a mixture of a molar excess of a fatty acid or fatty acid ester or a mixture thereof with a hydroxyalkyl sulfonate of the formula HOR'-$SO_3$M or aminoalkylsulfonate of the formula

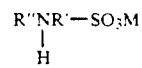

$$\underset{\underset{H}{|}}{R''N}R'-SO_3M$$

in the presence of a reaction promotor, at a temperature between about 200° to 250° C., in a substantially oxygen-free atmosphere, while removing water or alcohol of condensation formed during the reaction;
(b) rapidly distilling the reaction mixture under conditions sufficient to remove excess fatty acid or excess fatty acid ester while maintaining the fluidity of the reaction mixture;
(c) rapidly cooling the hot product to obtain a solid form of the compound of formula I with minimized color or product degradation.

2. The process of claim 1, wherein the molar ratio of said fatty acid or fatty acid ester to said hydroxyalkylsulfonate or aminoalkylsulfonate is between about 1.1:1 and 2:1.

3. The process of claim 1, wherein the fatty acids are derived from coconut oil.

4. The process of claim 1, wherein the hydroxyalkylsulfonate or aminoaklylsulfonate of step (a) is introduced in the form of an aqueous solution.

5. The process of claim 1, wherein the hydroxyalkyl sulfonate is sodium isethionate.

6. The process of claim 1, wherein the distillation step is conducted at between 0.1 and 50 mm Hg vacuum and between 200° and 300° C. temperature for between 0.5 and 10 hours.

7. The process of claim 6, wherein the distillation is conducted at between 1 and 10 mm Hg vacuum and between 240° and 290° C. temperature for between 1 and 4 hours.

8. The process of claim 1, wherein the cooling step is carried out on a belt flaker using water or glycol water as coolant at a temperature between 0° and 40° C.

9. The process of claim 8, wherein the water or glycol water is at a temperature between 10° and 20° C.

10. The process of claim 1, wherein the cooling step is carried out on a rotary drum flaker using cooling water, glycol water or a cryogenically-cooled liquid as coolant at a temperature between −45° and 40° C.

11. The process of claim 10, wherein the cooling is at a temperature between −30° 0 and 20° C.

12. The process of claim 11, wherein the cryogenically cooled liquid is d-limonene.

13. The process of claim 10, wherein the cryogenically cooled liquid is d-limonene.

14. In a process for preparing a compound of formula (I)

RCOXR'SO$_3$M     (I)

wherein:
R represents an aliphatic hydrocarbon residue of a fatty acid or a fatty acid ester containing from 6 to 24 carbon atoms,
R' represents a divalent hydrocarbon radical containing from 2 to 4 carbon atoms,
X represents oxygen or N-R" where R" represents hydrogen or a $C_1$-$C_7$ alkyl, and
M represents an alkali metal cation,
comprising:
heating a mixture of a molar excess of a fatty acid or fatty acid ester or a mixture thereof with a hydroxyalkyl sulfonate of the formula HOR'-SO$_3$M or aminoalkylsulfonate of the formula $$\begin{array}{c} R''NR'-SO_3M \\ | \\ H \end{array}$$

in the presence of a reaction promotor, at a temperature between about 200° to 250° C., in a substantially oxygenfree atmosphere, while removing water or alcohol of condensation formed during the reaction;
(a) the improvement which comprises distilling the reaction mixture to remove excess fatty acid or excess fatty acid ester in a thin film or wiped film evaporator at 50 mm Hg vacuum or less and between 200° and 300° C. at a ratio of feed per unit surface area of 10 to 75 pounds per sq. ft. hr; and
(b) rapidly cooling the hot product to obtain a solid form of the compound of formula I with minimized color or product degradation.

15. The process of claim 14, wherein the distillation is conducted at between 1 and 5 mm Hg vacuum and between 230° C. and 290° C. at a ratio of feed per unit surface area of 35 to 55 pounds per sq. ft. hr.

16. The process of claim 14, wherein the cooling step is carried out on a belt flaker using water or glycol water as coolant at a temperature between 0° and 40° C.

17. The process of claim 16, wherein the water or glycol water is at a temperature between 10° and 20° C.

18. The process of claim 14, wherein the cooling step is carried out on a rotary drum flaker using cooling water, glycol water or a cryogenically-cooled liquid as coolant at a temperature between −45° and 40° C.

19. The process of claim 18, wherein the cooling is at a temperature between −30° and 20° C.

20. The process of claim 18, wherein the cryogenically cooled liquid is d-limonene.

* * * * *